(12) United States Patent
Imamura et al.

(10) Patent No.: US 8,082,026 B2
(45) Date of Patent: Dec. 20, 2011

(54) HEARTBEAT DETECTING APPARATUS

(75) Inventors: Ayako Imamura, Anjo (JP); Mitsuhiro Ando, Toyohashi (JP); Shunsuke Kogure, Toyota (JP)

(73) Assignee: Aisin Seiki Kabushiki Kaisha, Aichi (JP)

( * ) Notice: Subject to any disclaimer, the term of this patent is extended or adjusted under 35 U.S.C. 154(b) by 275 days.

(21) Appl. No.: 12/441,071

(22) PCT Filed: Sep. 5, 2007

(86) PCT No.: PCT/JP2007/067318
§ 371 (c)(1),
(2), (4) Date: Mar. 12, 2009

(87) PCT Pub. No.: WO2008/038501
PCT Pub. Date: Apr. 3, 2008

(65) Prior Publication Data
US 2010/0056937 A1 Mar. 4, 2010

(30) Foreign Application Priority Data
Sep. 28, 2006 (JP) ................................. 2006-264858

(51) Int. Cl.
*A61B 5/04* (2006.01)
(52) U.S. Cl. ....................................... 600/509; 340/576

(58) Field of Classification Search .................. 340/573, 340/575, 576; 600/508, 509, 527
See application file for complete search history.

(56) References Cited

U.S. PATENT DOCUMENTS

| 5,404,128 A | * | 4/1995 | Ogino et al. | ............... 340/425.5 |
| 6,271,760 B1 | * | 8/2001 | Watanabe et al. | ............. 340/667 |
| 7,219,923 B2 | | 5/2007 | Fujita et al. | |
| 2006/0258915 A1 | * | 11/2006 | Ueda et al. | ..................... 600/301 |
| 2010/0018327 A1 | * | 1/2010 | Kogure et al. | ............ 73/862.041 |

FOREIGN PATENT DOCUMENTS

| JP | 07-204167 A | 8/1995 |
| JP | 2004-345617 A | 12/2004 |
| JP | 2005-110910 A | 4/2005 |

* cited by examiner

*Primary Examiner* — George Evanisko
*Assistant Examiner* — Mallika Fairchild
(74) *Attorney, Agent, or Firm* — Sughrue Mion, PLLC

(57) ABSTRACT

A heart beat sensor (10) comprises signal processing means (15) for performing frequency analysis of the output signal of a piezoelectric sensor (1) installed in a seat (2) and judging means (16) judges on the basis of the results of the frequency analysis that if the amplitude of the signal component in a first preset frequency range included in the output signal is in a preset amplitude range, the signal component includes a human body seating waveform indicating a person is seated in the seat (2).

10 Claims, 8 Drawing Sheets

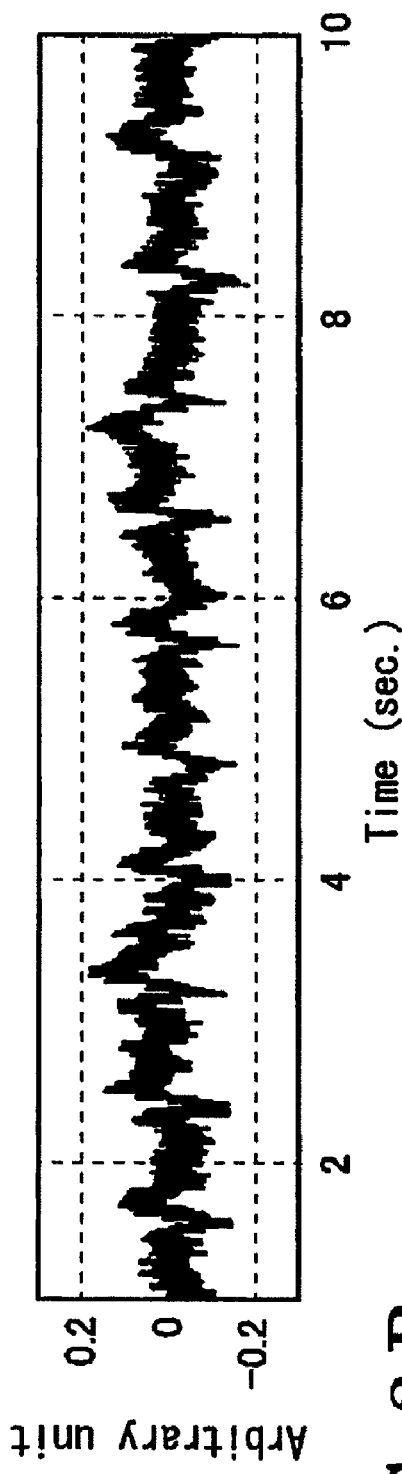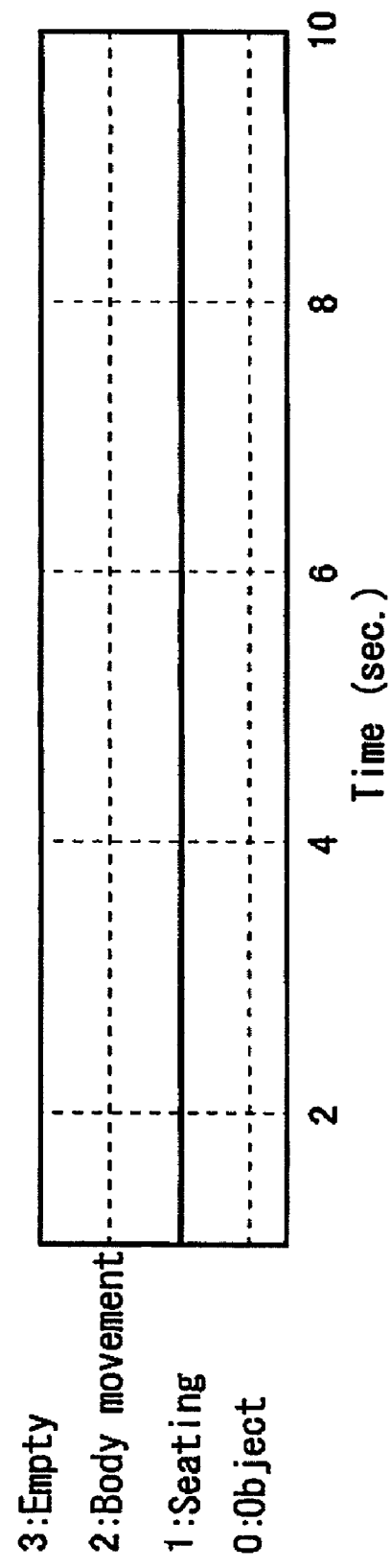

3: Empty
2: Body movement
1: Seating
0: Object

HEARTBEAT DETECTING APPARATUS

BACKGROUND OF THE INVENTION

1. Field of the Invention

The present invention relates to a heartbeat detecting apparatus that detects a heartbeat of a person seated on a seat based on output signals of piezoelectric sensors provided at the seat.

2. Description of the Invention

There is a heartbeat detecting apparatus for detecting a heartbeat of a person seated on a seat of a vehicle, such as an automobile. Heartbeat detecting apparatuses are categorized into an apparatus of constrained type, in which a sensor for detecting the heartbeat of the person is attached at an arm of the person, or the like, and an apparatus of unconstrained type, in which a sensor for detecting the heartbeat of the person is not attached at the person. The heartbeat detecting apparatus of constrained type surely detects the heartbeat when the sensor is attached at a predetermined position of the person. However, because a portion of the person is constrained, the person is prevented from moving freely and a drawback may occur that a subject feels that his/her heartbeat is being detected. On the other hand, the heartbeat detecting apparatus of unconstrained type is preferable in respect that the person is allowed to move freely and the subject does not feel that his/her heartbeat is being detected.

In a heartbeat detecting apparatus of unconstrained type according to patent publication 1, a piezoelectric sensor is provided at a seat of a vehicle. The piezoelectric sensor detects a pulse (i.e. a heartbeat) of a blood flow of a person seated on the seat. More specifically, a frequency analysis is executed on an output signal of the piezoelectric sensor and a power spectrum is calculated. The heartbeat of the person seated on the seat is detected by extracting a signal component corresponding to a heartbeat frequency, from the power spectrum.

Patent publication 1: JP2004-345617A

Such drawback may occur in the heartbeat detecting apparatus of the unconstrained type that the piezoelectric sensor outputs a signal based on a factor other than the heartbeat because the heartbeat detecting apparatus of unconstrained type does not constrain the person. For example, signal components resulted from, such as a movement of the person on the seat (a body movement) and a placement of an object on the seat, may be included in a frequency range of the heartbeat. Therefore, the heartbeat detecting apparatus according to patent publication 1 determines all the signal components among the output signals of the piezoelectric sensor corresponding to the heartbeat frequency to be the heartbeats. However, as described above, signals resulted from, such as the movement of the person and the placement of the object may be included in the signal components of the heartbeat. In particular, signals resulted from the placement of the object and a vibration of a vehicle in an idling state may be determined as the heartbeat signals. In other words, the heartbeat detecting apparatus according to patent publication 1 has a drawback that the heartbeat signal of the person is not precisely obtained because the heartbeat detecting apparatus determines the heartbeat signal without determining whether the occupant is seated on the seat or not.

An objective of the present invention is to provide a heartbeat detecting apparatus that detects whether an occupant is seated on a seat or not, based on an output signal of a piezoelectric sensor. A further objective of the present invention is to provide the heartbeat detecting apparatus that precisely obtains a signal component including a waveform of a heartbeat of the person, from the output signal of the piezoelectric sensor.

SUMMARY OF THE INVENTION

According to an aspect of a heartbeat detecting apparatus of the present invention for achieving the above-described objectives, the heartbeat detecting apparatus includes a signal processing device executing a frequency analysis on an output signal of a piezoelectric sensor provided at a seat and a determining device determining that the signal component includes a waveform of a seated person indicating that a person is seated on the seat, when an amplitude of a signal component, which is included in the output signal and which exists within a first predetermined frequency range, exists within a predetermined amplitude range, based on a result of the frequency analysis of the signal processing device.

According to the above-described aspect, the frequency analysis and an amplitude analysis are executed on the output signal of the piezoelectric sensor. In other words, by executing the frequency analysis on the output signal of the piezoelectric sensor, the signal component corresponding to the waveform of the seated person is obtained. The waveform of the seated person corresponds to the frequency resulted from, for example, a pulse of a blood flow (i.e. the heartbeat) or a breath of the person seated on the seat. Further, by considering that amplitudes of signal components differ from each other when the piezoelectric sensor detects the heartbeat of the person seated on the seat, a movement of the person on the seat and a placement of an object on the seat, the amplitude analysis is executed on the signal component existing within the first predetermined frequency range. Thus, signals generated by the placement of the object on the seat, by the movement of the person on the seat, and by a vibration of an idling vehicle are eliminated. Therefore, the heartbeat detecting apparatus is provided that surely obtains the signal component, including the waveform of the seated person indicating that the person is seated on the seat, from the output signal of the piezoelectric sensor.

According to another aspect of the heartbeat detecting apparatus of the present invention, when the determining device determines that the signal component includes the waveform of the seated person, the determining device determines that a potential heartbeat signal extracted from the output signal of the piezoelectric sensor is the heartbeat signal of the person.

According to the above-described aspect, the person is determined to be seated on the seat. Therefore, the potential heartbeat signal extracted form the output signal of the piezoelectric sensor is surely the heartbeat signal of the person. Therefore, the signal component including the waveform of the heartbeat of the person is accurately obtained form the output signal of the piezoelectric sensors.

According to another aspect of the heartbeat detecting apparatus of the present invention, the piezoelectric sensor is a plurality of piezoelectric sensors provide at the seat.

According to the above-described aspect, the plurality of piezoelectric sensors is provided on the seat. Therefore, in whatever state the person is seated on the seat, the waveform of the heartbeat of the person is more likely to be detected by any one of the plurality of piezoelectric sensors.

According to another aspect of the heartbeat detecting apparatus of the present invention, the signal processing device executes the frequency analysis separately on the respective output signals of the plurality of piezoelectric sensors, and when each of equal to or more than two of the potential heartbeat signals extracted from each of equal to or more than two of the signal components, which is included in each of the output signals of equal to or more than two of the piezoelectric sensors among the plurality of piezoelectric sensors and which exists within the second predetermined frequency range, exists during a predetermined time frame, and when each of the signal components, which is included in each of the output signals of equal to or more than two of the piezoelectric sensors and which exists within the first predetermined frequency range, is determined to include the waveform of the seated person, based on the result of the frequency analysis of the signal processing device on each of the output signals, the determining device is configured to determine that at least one of equal to or more than two of the potential heartbeat signals is the heartbeat signal of the person.

According to the above-described aspect, when the person is determined to be seated on the seat and when the potential heartbeat signals obtained by the plurality of piezoelectric sensors exist within the predetermined time frame, the determining device determines that at least one of the potential heartbeat signals is not to be a noise but to be the heartbeat signal resulted from the pulse of the blood flow (i.e. the heartbeat) of the person seated on the seat.

According to another aspect of the heartbeat detecting apparatus of the present invention, the signal processing device executes the frequency analysis separately on the respective output signals of plurality of piezoelectric sensors, and, when each of equal to or more than two of the potential heartbeat signals extracted from each of equal to or more than two of the signal components, which is included in each of the output signals of equal to or more than two of the piezoelectric sensors among the plurality of piezoelectric sensors and which exists within the second predetermined frequency range, exists during a predetermined time frame, and when each of the signal components, which is included in each of the output signals of equal to or more than two of the piezoelectric sensors and which exists within the first predetermined frequency range, is determined to include the waveform of the seated person, based on the result of the frequency analysis of the signal processing device on each of the output signals, the determining device is configured to determine that each of equal to or more than two of the potential heartbeat signals is the heartbeat signal of the person.

According to the above-described aspect, when the person is determined to be seated on the seat and when the potential heartbeat signals obtained by the plurality of piezoelectric sensors exist within the predetermined time frame, the determining device determines that each of the potential heartbeat signals is not to be the noise but to be the heartbeat signal resulted from the pulse of the blood flow (i.e. the heartbeat) of the person seated on the seat. Thus, by comparing the potential heartbeat signals obtained by the piezoelectric sensors, whether the potential heartbeat signals are the heartbeat signals of the person or not is accurately determined.

According to another aspect of the heartbeat detecting apparatus of the present invention, the signal processing device executes the frequency analysis separately on the respective output signals of plurality of piezoelectric sensors, and when a second potential heartbeat signal extracted from a second signal component, which is included in the output signal of a second piezoelectric sensor among the plurality of piezoelectric sensors and which exists within a second predetermined frequency range, exists during the predetermined time frame before and/or after a peak time of a first potential heartbeat signal, which is extracted from a first signal component included in the output signal of the first piezoelectric sensor among the plurality of piezoelectric sensors and existing within the second predetermined frequency range, and when the signal components, which are included in the output signals of the first and second piezoelectric sensors and which exist within the first frequency range, includes the waveform of the seated person, based on a result of the frequency analysis of the signal processing device executed on each of the output signals of the plurality of piezoelectric sensors, the determining device is configured to determine that the first potential heartbeat signal is the heartbeat signal of the human body.

According to the above-described aspect, when the person is determined to be seated on the seat and when the second potential heartbeat signal obtained by the second piezoelectric sensor exists within the predetermined time frame after the peak time of the first potential heartbeat signal obtained by the first piezoelectric sensor among the plurality of piezoelectric sensors, the determining device determines that the first potential heartbeat signal is not to be the noise but to be the heartbeat signal resulted from the pulse of the blood flow (i.e. the heartbeat) of the person seated on the seat. Thus, by comparing the potential heartbeat signals obtained by the plurality of piezoelectric sensors, whether the potential heartbeat signals are the heartbeat signals of the person or not is accurately determined.

According to another aspect of the heartbeat detecting apparatus of the present invention, the signal processing device executes the frequency analysis separately on the respective output signals of plurality of piezoelectric sensors, and when a second potential heartbeat signal extracted from a second signal component which is included in the output signal of a second piezoelectric sensor among the plurality of piezoelectric sensors and which exists within a second predetermined frequency range, exists during the predetermined time frame before and/or after a peak time of a first potential heartbeat signal, which is extracted from a first signal component included in the output signal of the first piezoelectric sensor among the plurality of piezoelectric sensors and existing within the second predetermined frequency range, and when the signal components which are included in the output signals of the first and second piezoelectric sensors and which exist within the first frequency range, includes the waveform of the seated person, based on a result of the frequency analysis of the signal processing device executed on each of the output signals of the plurality of piezoelectric sensors, the determining device is configured to determine that the second potential heartbeat signal is the heartbeat signal of the human body.

According to the above-described aspect, when the person is determined to be seated on the seat and when the second potential heartbeat signal obtained by the second the piezoelectric sensor exists within the predetermined time frame after the peak time of the first potential heartbeat signal obtained by the first piezoelectric sensor among the plurality of piezoelectric sensors, the determining device determines that the second potential heartbeat signals is not to be the noise but to be the heartbeat signal resulted from the pulse of the blood flow (i.e. the heartbeat) of the person seated on the seat. Thus, by comparing the potential heartbeat signals obtained by the plurality of piezoelectric sensors, whether the potential heartbeat signals are the heartbeat signals of the person or not is accurately determined.

According to another aspect of the heartbeat detecting apparatus of the present invention, the signal processing device executes the frequency analysis separately on the respective output signals of plurality of piezoelectric sensors, when each of equal to or more than two of each of the signal components, which is included in each of the output signals of equal to or more than two of the piezoelectric sensors among the plurality of piezoelectric sensors and which exists within a second predetermined frequency range, exists during a predetermined time frame, and when each of the signal components, which is included in each of the output signals of equal to or more than two of the piezoelectric sensors and which exists within the first predetermined frequency range, is determined to include the waveform of the seated person, based on the results of the frequency analysis of the signal processing device on each of the output signals, the determining device is configured to determine that each of equal to or more than two signal components is the heartbeat signal of the person, and the determining device is configured so that, when the heartbeat signal detected by another piezoelectric sensor exists during a predetermined time frame before and/or after a peak time of the heartbeat signal detected by the base piezoelectric sensor, the determining device provides a point to the base piezoelectric sensor and the other piezoelectric sensor so that the point is accumulated in the piezoelectric sensors, and the determining device outputs the heartbeat signal based on the output signal of the piezoelectric sensor in which the highest score is accumulated.

According to the above-described aspect, the highest score is accumulated in the piezoelectric sensor that detects the heartbeat signals of the person for a great number of times. By executing scoring of each of the piezoelectric sensors, it is determined which piezoelectric sensor among the plurality of piezoelectric sensors frequently detects the heartbeat signals of the person. Therefore, when one piezoelectric sensor among the plurality of piezoelectric sensors needs to be used, by using the piezoelectric sensor in which the highest score is accumulated, the heartbeat signals of the person is more likely to be detected.

BRIEF DESCRIPTION OF DRAWINGS

FIG. 2A is a diagram illustrating an output signal of a piezoelectric sensor;

FIG. 2B is a diagram illustrating a result obtained by executing a seating condition determination;

DETAILED DESCRIPTION OF THE EMBODIMENTS

First Embodiment

Figure 1:
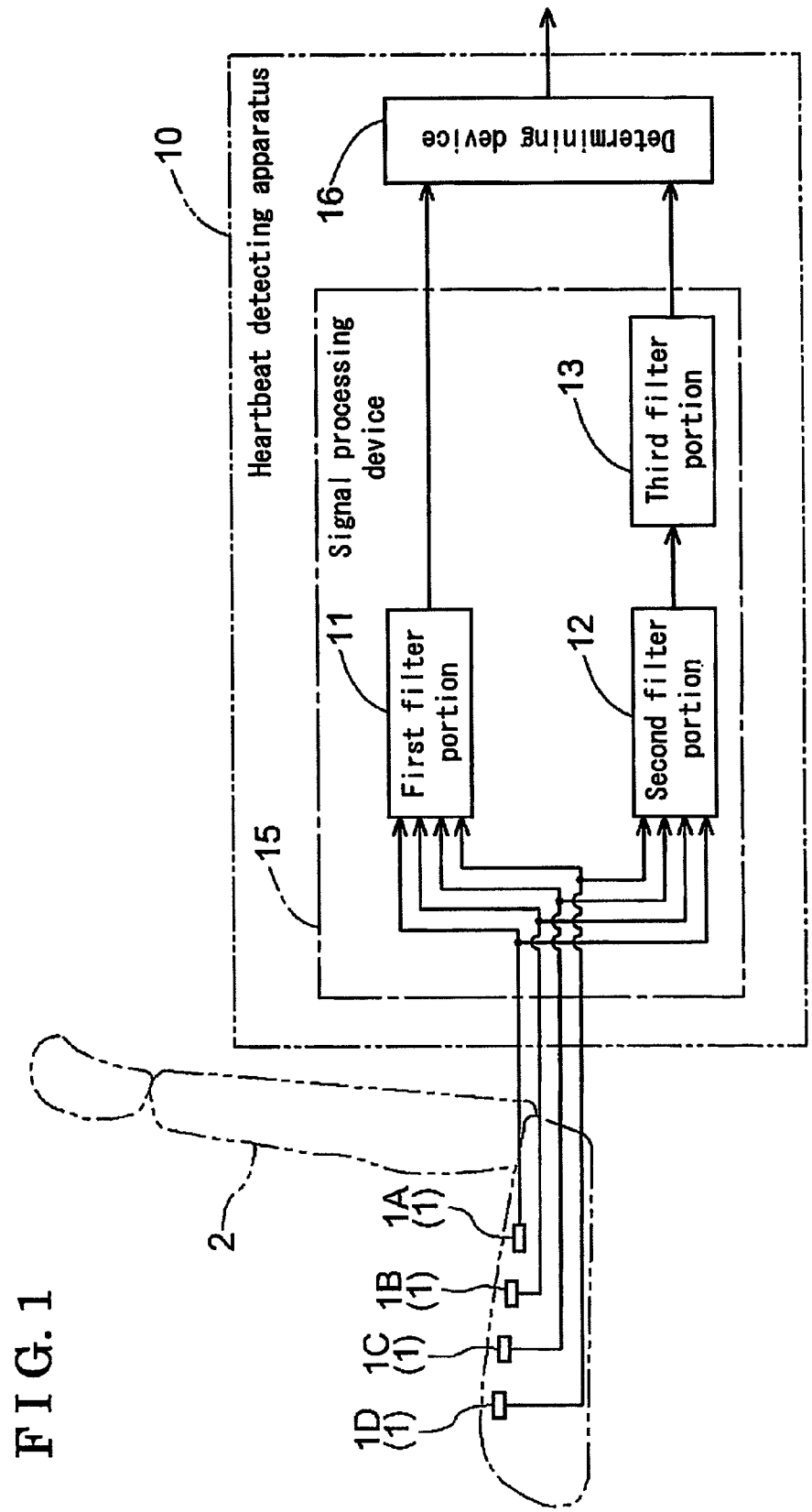
FIG. 1 is a block diagram illustrating a function of a heartbeat detecting apparatus according to a first embodiment.

A heartbeat detecting apparatus 10 according to the present invention will be described hereinbelow with reference to the attached drawings. An objective of the heartbeat detecting apparatus 10 according to the present invention is to detect a heartbeat of a person seated on a seat 2. A sensor of unconstrained type is adapted at the heartbeat detecting apparatus 10 in order to allow a subject to move freely and in order for the subject not to feel that his/her heartbeat is detected. More specifically, piezoelectric sensors 1 (1A-1D) of unconstrained type illustrated in FIG. 1 are provided at a seating portion of the seat 2. A plurality of piezoelectric sensors 1A-1D are provided at the seat 2, and therefore wherever the person is seated on the seat 2, the heartbeat of the person is detected. The piezoelectric sensors 1A-1D may be provided at a backrest portion of the seat 2, or the like, as long as the heartbeat of the person is detected.

FIG. 1 is a block diagram illustrating a function of the heartbeat detecting apparatus 10 according to the first embodiment. The heartbeat detecting apparatus 10 includes a signal processing device 15 and a determining device 16. The signal processing device 15 executes a frequency analysis on output signals of the piezoelectric sensors 1 provided at the seat 2. When amplitude of a signal component, which is included in the output signals and which exists within a predetermined frequency range (which serves as a first predetermined frequency range of the invention), exists within a predetermined amplitude range, the determining device 16 determines that the signal component include a waveform of a seated person indicating that the person is seated on the seat 2 (the person seated on the seat 2 is in a substantially still state), based on a result of the frequency analysis of the signal processing device 15. Further, the signal processing device 15 may be modified to execute an amplification processing on the output signals of the piezoelectric sensors 1. Furthermore, the signal processing device 15 and the determining device 16 may separately process the output signals of the plurality of piezoelectric sensors 1A, 1B, 1C and 1D.

Figure 3A:
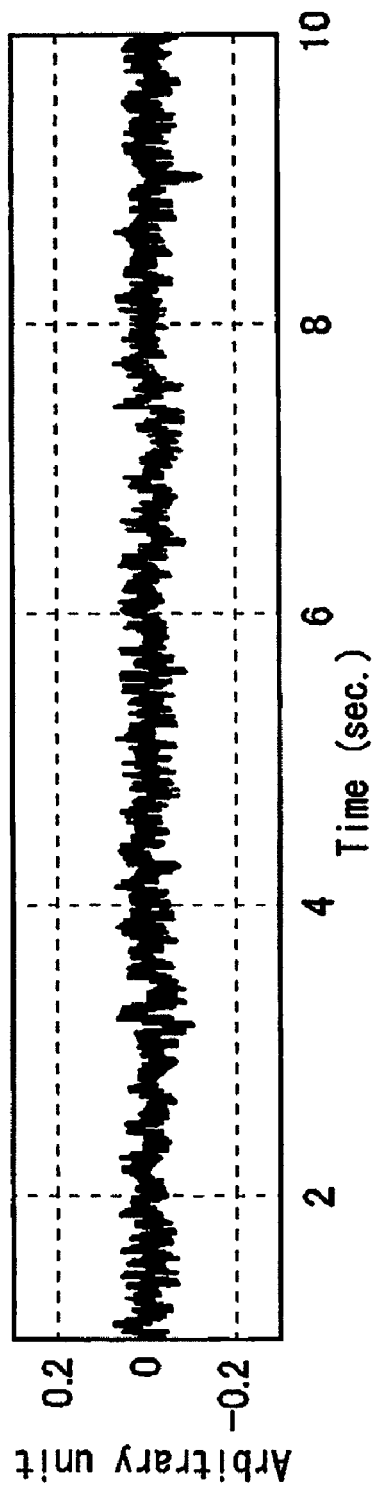
FIG. 3A is a diagram illustrating an output signal of a piezoelectric sensor.

FIG. 2A is a diagram illustrating the output signal of the single piezoelectric sensor 1 that is inputted into the signal processing device 15. FIG. 3A is a diagram illustrating the output signal of another piezoelectric sensor 1 that is inputted into the signal processing device 15. The diagrams in FIG. 2A and FIG. 3A are obtained at the same time frame but waveforms of signals differ from each other. The output signals are obtained when the person is seated on the seat 2.

The piezoelectric sensors 1 are provided at the seat 2. Therefore, when the seat 2 is vibrated and the vibration is transmitted to the piezoelectric sensors 1, output signals corresponding to a frequency and an amplitude of the vibration are outputted from the piezoelectric sensors 1. The seat 2 is vibrated when there is the pulse of a blood flow of the person (i.e. the heartbeat) seated on the seat 2, when the person sits on the seat 2, when the person stands up from the seat 2, when the person moves while seated, when an object is placed on the seat 2, and the like. In a case where the seat 2 is adapted on a vehicle, such as an automobile, a vibration of the vehicle itself (for example, a vibration of the vehicle in an idling state) may cause the vibration of the seat 2.

The signal processing device 15 of the heartbeat detecting apparatus 10 executes the frequency analysis on the output signals of the piezoelectric sensors 1 in order to distinguish signal components, which exist within the predetermined frequency range corresponding to a frequency range of the waveform of the seated person, from the output signals of the piezoelectric sensors 1.

Signal components resulted from the person sits on the seat 2, the person Stands up from the seat 2, the person moves while seated, the object is placed on the seat 2, and the vehicle in the idling state vibrates, may be included within the predetermined frequency range. However, when the signal components have different origins, strength of the signal components, that is, amplitudes of the signal components differ. For example, an amplitude of the signal component resulted from a vibration generated when the person sits on the seat 2, an amplitude of the signal component resulted from a vibration generated when the person stands up from the seat 2, and an amplitude of the signal component resulted from a vibration generated when the person moves while seated are extremely high. On the other hand, an amplitude of the signal component corresponding to the waveform of the seated person indicating the person is seated on the seat 2, is relatively low. When the amplitude of the signal component, which is included in the output signals of the piezoelectric sensors 1 and which exists within the predetermined frequency range, exists within the predetermined amplitude range, the determining device 16 determines that the signal component includes the waveform of the seated person indicating that the person is seated on the seat 2 based on the result of the frequency analysis of the signal processing device 15. Thus, the determining device 16 executes the amplitude analysis based on the output signals of the piezoelectric sensors 1.

As illustrated in FIG. 1, the signal processing device 15 executes a signal processing on the output signals of the piezoelectric sensors 1 by means of a first filter portion 11 in parallel with signal processing on the output signals of the piezoelectric sensors 1 by means of a second filter portion 12 and a third filter portion 13. Based on a result of the signal processing by means of the first filter portion 11 and on results of the signal processing by means of the second and third filter portions 12 and 13, the determining device 16 determines whether the person is seated on the seat 2 or not.

The first filter portion 11 executes the frequency analysis for filtering and eliminating a signal component existing within a frequency range of an idling of the vehicle where the seat 2 is adapted (for example, equal to or more than 10 Hz) from the output signals. When neither the person nor the object exists on the seat 2, amplitudes of the signal component, after the signal processing executed by the first filter portion 11, are extremely low. On the other hand, when the person, the object, or the like exists on the seat 2, the amplitudes of the signal component after the signal processing executed by the first filter portion 11 is high to some extent. Therefore, based on the result of the signal processing of the first filter portion 11, by analyzing the amplitudes of the signal components after the signal processing of the filter portion 11, the determining device 16 determines whether the seat 2 is empty or the seat 2 is occupied by the person, the object, or the like.

As described above, the frequency analysis and the amplitude analysis are executed on the output signals of the piezoelectric sensors 1 by means of the first filter portion 11 of the signal processing device 15 and the determining device 16.

The second filter portion 12 executes the frequency analysis in order to filter and extract a signal component existing within a predetermined frequency range corresponding to a frequency range of the heartbeat, from the output signals. The third filter portion 13 executes the frequency analysis in order to filter and extract a signal component existing within a predetermined frequency range that is lower than the frequency range of the heartbeat. Therefore, the signal component outputted from the third filter portion 13 is the signal component whose frequency range is lower than the frequency range of the heartbeat. In such frequency range, a frequency of the waveform of the seated person is included which indicates that the person is seated on the seat 2, such as a breathing of the person. The signal component outputted after processing of the second and third filter portions 12 and 13 is the signal component that includes the frequency existing within the first predetermined frequency range of the present invention.

As described above, the frequency analysis and the amplitude analysis are executed on the output signals of the piezoelectric sensors 1 by means of the second and third filter portions 12 and 13 of the signal processing device 15 and the determining device 16.

A detailed description of the processing executed by the heartbeat detecting apparatus 10 according to the first embodiment will be provided hereinbelow. The determining device 16 determines that nothing exists on the seat 2 when the amplitude of the signal component after the signal processing of the first filter portion 11 is less than a first threshold value. In other words, the determining device 16 determines that the piezoelectric sensors 1 do not detect vibrations other than the vibration of the frequency eliminated by the first filter portion 11 and resulted from the idling. That is, the determining device 16 detects that the seat 2 is in an empty state. On the other hand, the determining device 16 determines that the person, the object, or the like exits on the seat 2 when the amplitudes of the signal component after the signal processing of the first filter portion 11 is equal to or more than the first threshold value. As will be described hereinbelow, the second and third filter portions 12 and 13 execute the signal processing in order to analyze what exists on the seat 2, for example the person or the object.

Figure 4A:
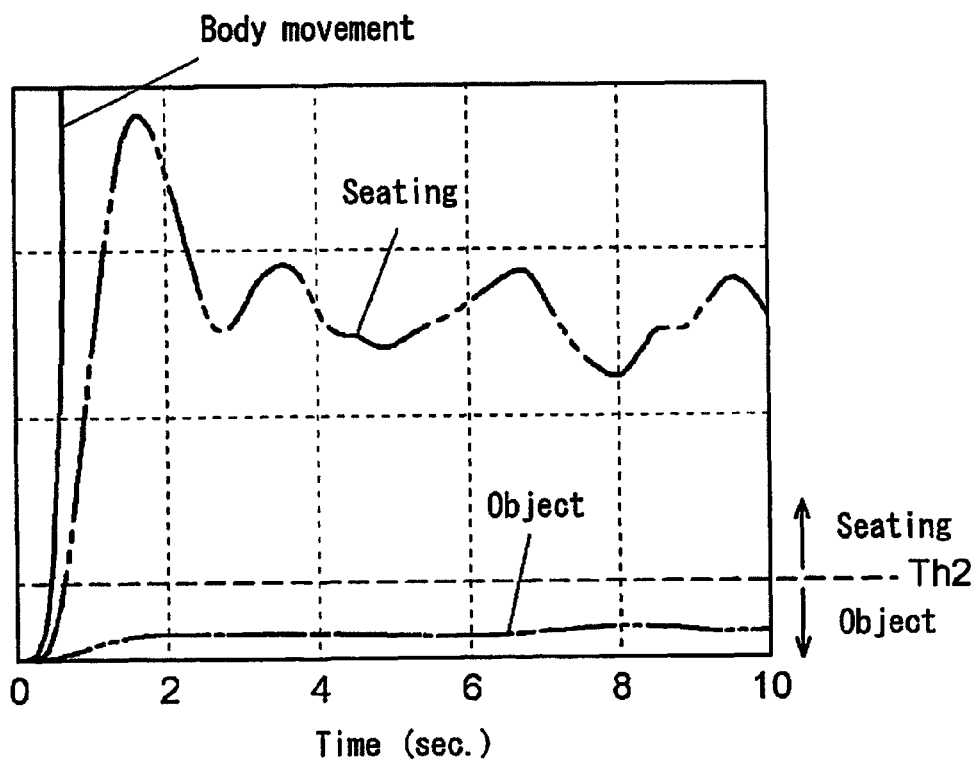
FIG. 4A is a diagram illustrating waveforms of signal components after a signal processing (a frequency analysis) is executed on an output signal of the piezoelectric sensor by a second filter portion and a third filter portion.
Figure 4B:
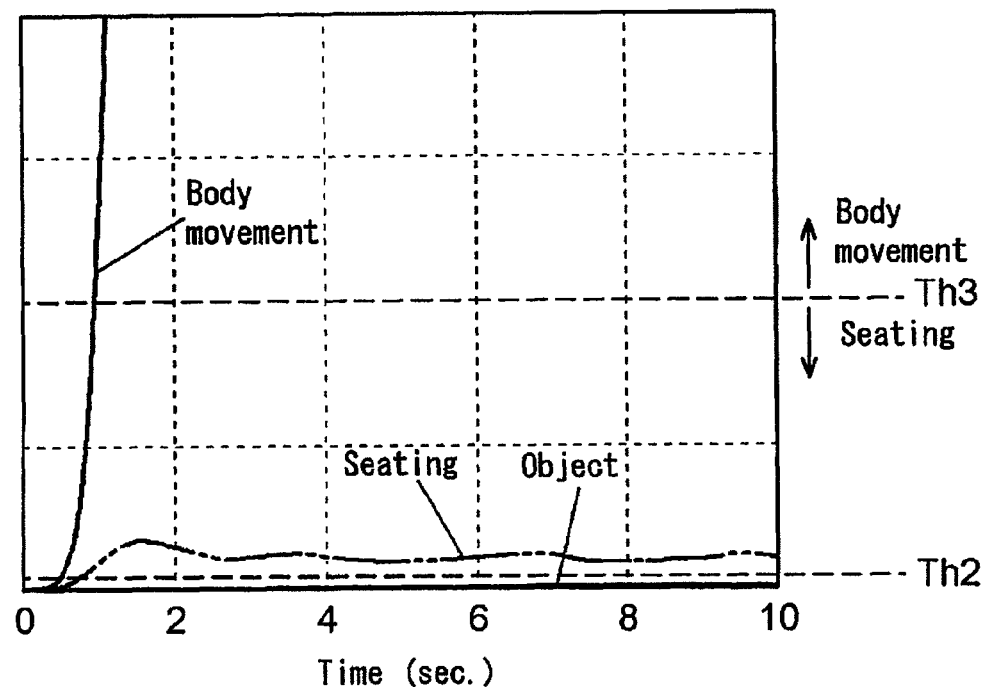

FIGS. 4A and 4B are diagrams illustrating waveforms of the signal components after the signal processing (the frequency analysis) executed on the output signal outputted form the piezoelectric sensor 1 of FIG. 2A by means of the second and third filter portions 12 and 13. FIG. 4A and FIG. 4B differ from each other only in a scale of longitudinal axes.

When the amplitude of the signal component after the signal processing of the second and third filter portions 12 and 13 exists within a predetermined amplitude range whose upper limit is defined by a second threshold value Th2, the determining device 16 determines that (executes the amplitude analysis so that) the object exists on the seat 2. Further, when the amplitude of the signal component after the signal processing of the second and third filter portions 12 and 13, exists within a predetermined amplitude range whose lower limit is defined by a third threshold value Th3, the determining device 16 determines that (executes the amplitude analysis so that) the person moves on the seat 2. Furthermore, when the amplitude of the signal component after the signal processing of the second and third filter portions 12 and 13 exists within a predetermined amplitude range whose lower limit is defined by the second threshold value Th2 and whose upper limit is defined by the third threshold value Th3, the determining device 16 determines that (executes the amplitude analysis so that) the person is seated on the seat 2.

The conventional heartbeat detecting apparatus does not determine whether the person is seated on the seat 2 based on the output signal of the piezoelectric sensor 1. However, as described above, the heartbeat detecting apparatus 10 according to the present invention determines whether the person is seated on the seat 2 based on the output signals of the piezoelectric sensors 1. Therefore, a signal component that includes the waveform of the seated person is accurately obtained from the output signals of the piezoelectric sensors 1.

Figure 3B:
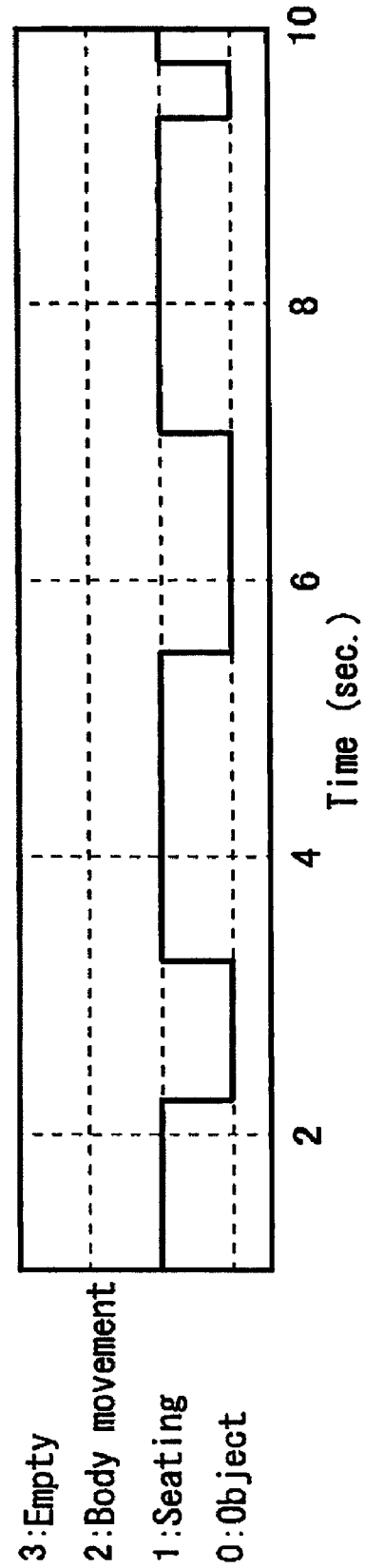
FIG. 3B is a diagram illustrating a result obtained by executing a seating condition determination.

FIG. 2B and FIG. 3B are diagrams illustrating results of a seating condition determination executed by the determining device 16 on the signal components after the signal processing (the frequency analysis) of the first, second and third filter portions 11, 12 and 13 (the waveforms illustrated in FIGS. 4A and 4B). The determining device 16 determines, whether the object is detected on the seat 2, whether the seating of the person on the seat 2 is detected, whether the movement of the person on the seat 2 is detected or whether the seat 2 is empty, based on the results of the frequency analysis and the amplitude analysis on the output signals of the piezoelectric sensors 1. While the seating is always detected from the output signal of the piezoelectric sensor 1 in FIG. 2A, the seating is discontinuously detected from the output signal of the piezoelectric sensor 1 in FIG. 3A. Therefore, the seating of the person is not appropriately detected from the output signal of the piezoelectric sensor 1 in FIG. 3A. Accordingly, even when attempting to detect the heartbeat signals from the piezoelectric sensor 1, the heartbeat is not accurately detected.

Second Embodiment

Figure 5:
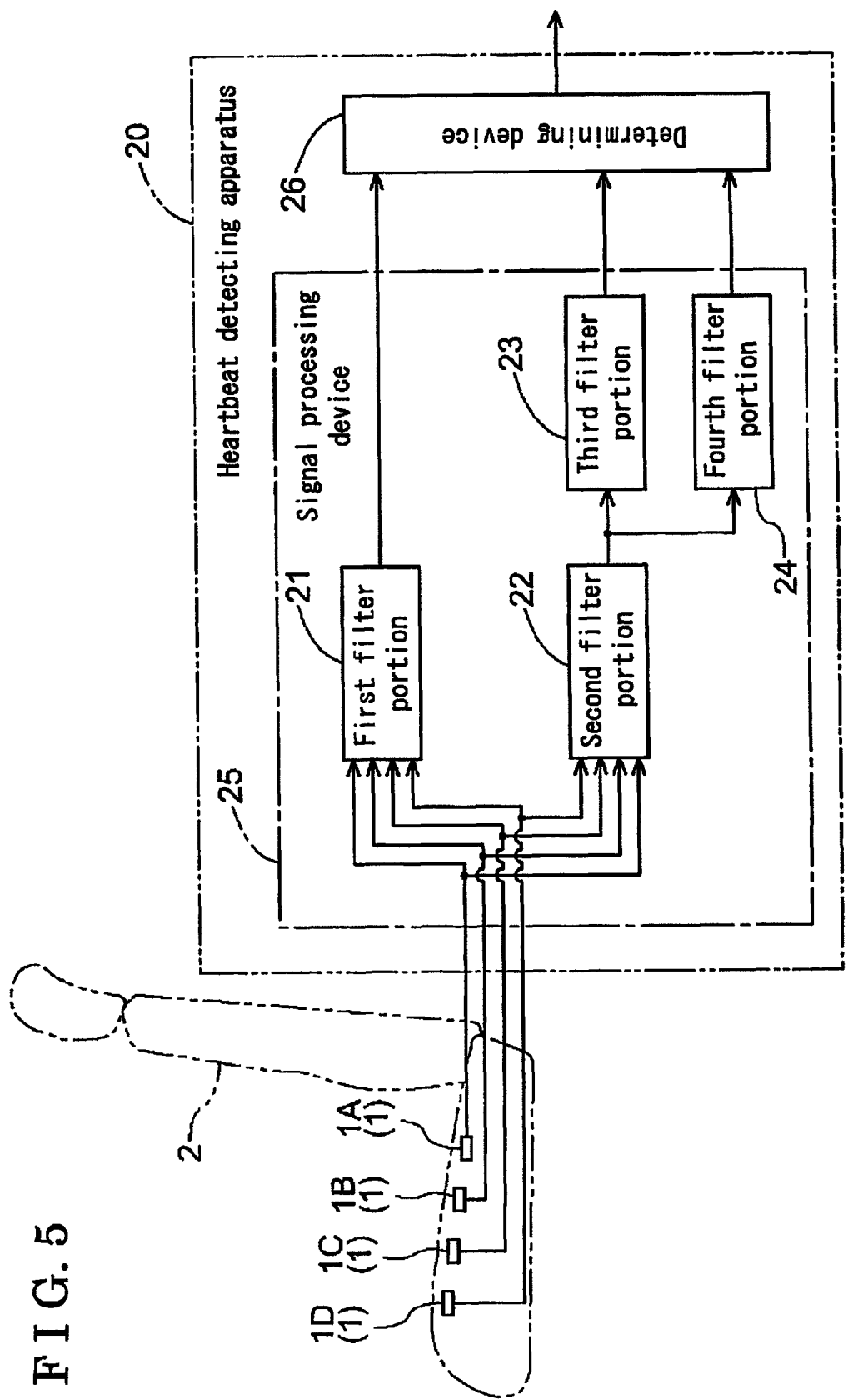
FIG. 5 is a block diagram illustrating a function of a heartbeat detecting apparatus according to a second embodiment.

A heartbeat detecting apparatus 20 according to a second embodiment is different from the heartbeat detecting apparatus 10 according to the first embodiment in that the heartbeat detecting apparatus 20 according to the second embodiment executes a processing in which output signals of plurality of piezoelectric sensors 1A, 1B, 1C and 1D are compared. FIG. 5 is a block diagram illustrating a function of the heartbeat detecting apparatus 20 according to the second embodiment. The heartbeat detecting apparatus 20 includes a signal processing device 25 and a determining device 26. The signal processing device 25 executes a frequency analysis on output signals of the piezoelectric sensors 1 (1A, 1B, 1C, 1D) provided at a seat 2. The determining device 26 determines whether a person is seated on the seat 2 and whether potential heartbeat signals, extracted from the output signals of the piezoelectric sensors 1, are a heartbeat of the person, based on a result of the frequency analysis of the signal processing device 25. As well as the first embodiment, the signal processing device 25 includes first, second and third filter portions 21, 22 and 23. Functions of the first, second and third filter portions 21, 22, and 23 are the same as functions of the first, second and third filter portions 11, 12, and 13 according to the first embodiment. The signal processing device 25 executes the frequency analysis on each of the output signals of the piezoelectric sensors 1. The determining device 26 determines whether an object is detected on the seat 2, whether a seating of the person on the seat 2 is detected, whether a movement of the person on the seat 2 is detected, or whether the seat 2 is empty, based on results of the frequency analysis and the amplitude analysis on the output signals of the piezoelectric sensors 1. A fourth filter portion 4 according to the present embodiment executes a smoothing and a zero cross point extraction on signal components existing within a frequency range corresponding to a waveform of the heartbeat and obtained by the frequency analysis of the second filter portion 22. Signal components, extracted by signal processing of the second filter portion 22 and the fourth filter portion 24, are the signal components that include a frequency within a second predetermined frequency range of the present invention.

Figure 6A:
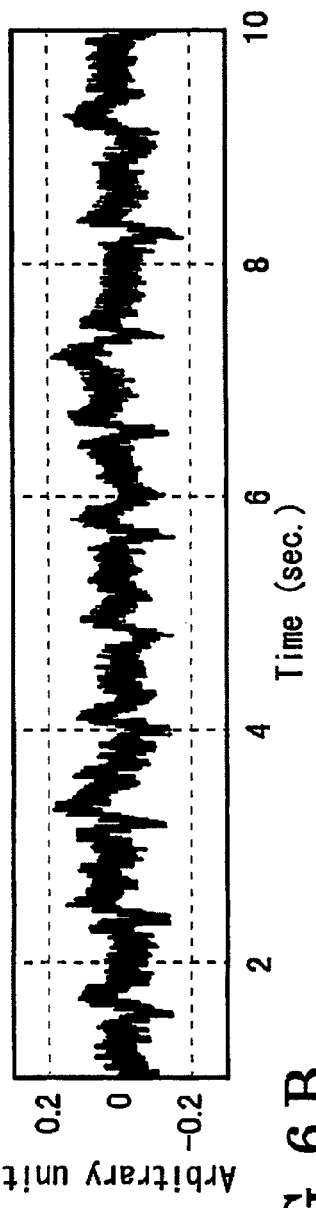
FIG. 6A is a diagram illustrating an output signal of a piezoelectric sensor.
Figure 6B:
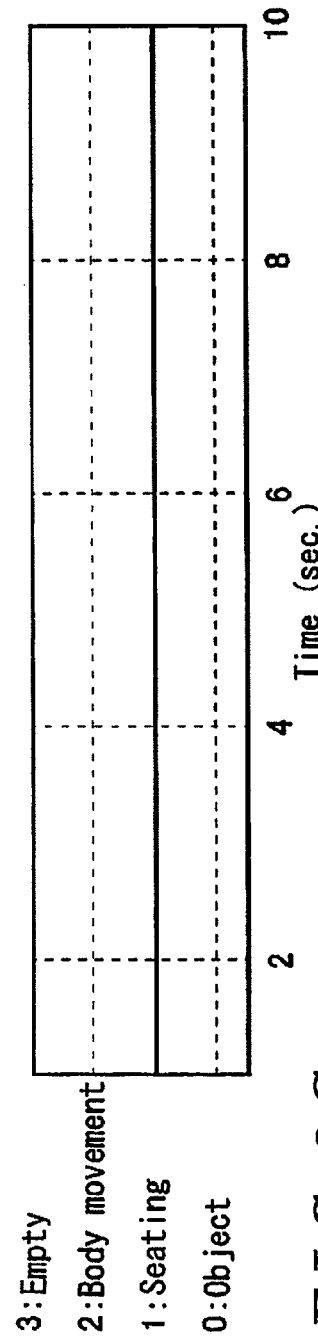
FIG. 6B is a diagram illustrating a result obtained by executing a seating condition determination.

FIG. 6A is a diagram illustrating the output signal of the single piezoelectric sensor 1 that is inputted into the signal processing device 25. FIG. 6B is a diagram illustrating a result of a seating condition determination, executed in the same manner as the first embodiment, on the output signal after the signal processing (the frequency analysis) by means of the second and third filter portions 22 and 23. These diagrams are the same as the diagrams in FIGS. 2A and 2B.

Figure 6C:
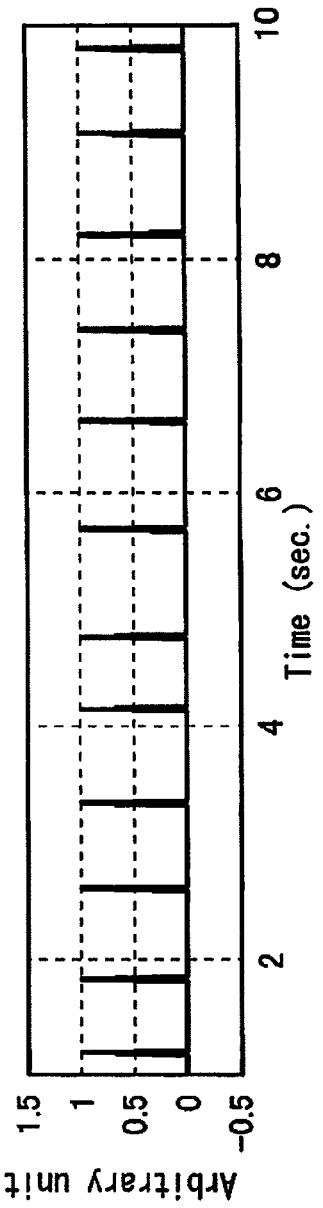
FIG. 6C is a diagram illustrating a potential heartbeat signal obtained by executing a signal processing by a second filter portion and a fourth filter portion.

FIG. 6C is a diagram illustrating potential heartbeat signals obtained by the signal processing (the frequency analysis) by means of the second and fourth filter portions 22 and 24. More specifically, the fourth filter portion 24 executes the smoothing on the signal components after the frequency analysis of the second filter portion 22 and then extracts the zero cross point (i.e. extracts the potential heartbeat signals). In other words, FIG. 6C is a diagram illustrating the potential heartbeat signals included in the output signal of the piezoelectric sensor 1.

The output signals of the plurality of piezoelectric sensors 1A, 1B, 1C and 1D provided at the seat 2 are inputted into the signal processing device 25. The same number of data of potential heartbeat signals as illustrated in FIG. 6C as the number of the piezoelectric sensors 1A, 1B, 1C and 1D are obtained. More specifically, the signal processing device 25 of the heartbeat detecting apparatus 20 according to the second embodiment executes the frequency analysis on each of the plurality of piezoelectric sensors 1A, 1B, 1C and 1D, and the data of the potential heartbeat signals after the signal processing are inputted into the determining device 26.

The above-described potential heartbeat signals are extracted regardless of the results of the determination of seating of the person on the seat 2. Therefore, the signals may be resulted from a movement generated on the seat 2 by the person or from a vibration of the object generated on the seat 2. In the same manner described above, according to the second embodiment, when the output signal of the piezoelectric sensor 1, by which the potential heartbeat signal is detected, is determined to include a waveform of the seated person, the determining device 26 determines that the potential heartbeat signal extracted from the piezoelectric sensor 1 is the heartbeat signal, based on results of the frequency analysis and the amplitude analysis of the second filter portion 22, third filter portion 23, and the determining device 26. Therefore, the heartbeat signal is more accurately detected.

Further, a manner described hereinbelow may be used in order to determine that the potential heartbeat signal is the heartbeat signal.

Figure 7:
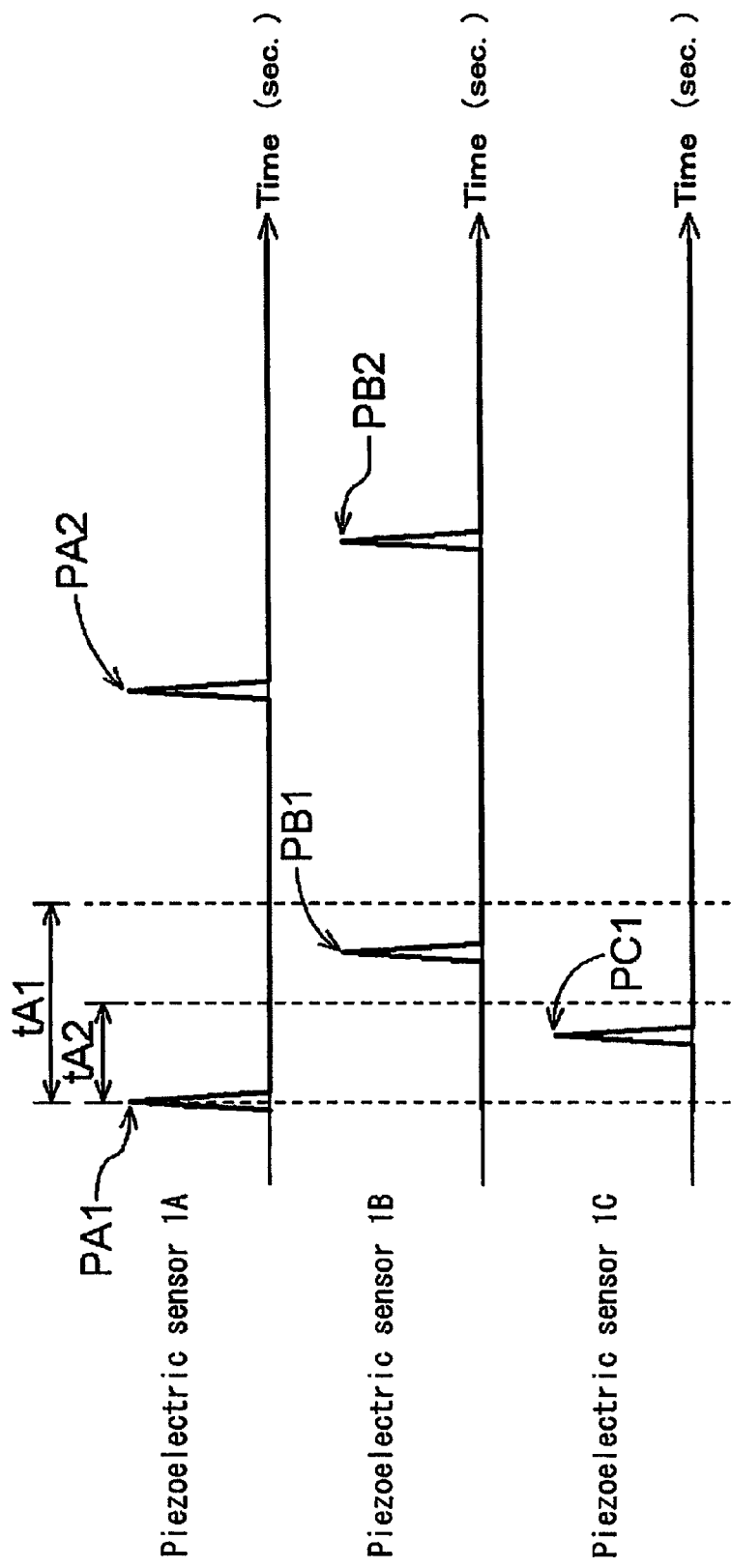
FIG. 7 is a diagram of data on potential heartbeat signals included in output signals of the plurality of piezoelectric sensors provided at the seat, illustrated by each of the piezoelectric sensors.

FIG. 7 is a diagram of data on the potential heartbeat signals included in the output signals of the plurality of piezoelectric sensors 1A, 1B, 1C and 1D provided at the seat 2, illustrated by each of the piezoelectric sensors 1 (1A, 1B, 1C and 1D). In FIG. 7, data only on the piezoelectric sensors, 1A, 1B and 1C are illustrated. The data on the potential heartbeat signals is inputted from the signal processing device 25 into the determining device 26. In order to extract the heartbeat signals from the output signals of the piezoelectric sensors 1 more accurately, the manner of comparing the output signals of the piezoelectric sensors 1 may be used. In other words, in a case where the potential heartbeat signals, resulted from the same heartbeat (i.e. the same pulse of a blood flow), are detected by the plurality of piezoelectric sensors 1A, 1B, 1C and 1D, the potential heartbeat signals are determined to be the heartbeat signals.

Therefore, according to the heartbeat detecting apparatus 20 of the second embodiment, when equal to or more than two of the potential heartbeat signals extracted from the signal components, which are included in the output signals of equal to or more than two of the piezoelectric sensors 1 among the plurality of piezoelectric sensors 1A, 1B, 1C and 1D and which exist within a predetermined frequency range (which serves as a second predetermined frequency range of the present invention), exist during a predetermined time frame, and when the signal components, which are included in equal to or more than two of the output signals of the piezoelectric sensors 1 and which exist within a predetermined frequency range (which serves as a first predetermined frequency range according to the present invention), include the waveform of the seated person, the determining device 26 determines that at least one of two potential heartbeat signals is the heartbeat, based on the results of the frequency analysis of the signal processing device 25 on each of the output signals.

More specifically, as illustrated in FIG. 7, the piezoelectric sensor 1A detects a potential heartbeat signal PA1 and a potential heartbeat signal PA2. The piezoelectric sensor 1B detects a potential heartbeat signal PB1 and a potential heartbeat signal PB2. The piezoelectric sensor 1C detects a potential heartbeat signal PC1. The determining device 26 uses the piezoelectric sensor 1A, which outputs the potential heartbeat signal PA1 detected earliest in terms of time, as a base. In a case where another potential heartbeat signal is detected by another piezoelectric sensor 1 during a predetermined time frame: tA1 after a peak time of the potential heartbeat signal PA1, the determining device 26 determines that the potential heartbeat signals are the heartbeat signals. The potential heartbeat signals are detected by the piezoelectric sensors 1 outputting the signal components that are determined to include the waveform of the seated person based on the results of the frequency analysis and the amplitude analysis by means of the second and third filter portions 22 and 23 and the determining device 26.

When each of peak times of equal to or more than two of waveforms of each of the signal components which are included in the each of output signals of equal to or more than two of the piezoelectric sensors 1 among the plurality of piezoelectric sensors 1A, 1B, 1C and 1D and which exist within the predetermined frequency range (the second predetermined frequency range) (i.e. the potential heartbeat signals), exists during the same time frame: tA1, and when each of the signal components, which is included in each of the output signals equal to or more than two piezoelectric sensors 1 and which exists within the predetermined frequency range (the first predetermined frequency range), is determined to include the waveform of the seated person, the determining device 26 determines that the each of equal to or more than two signal components includes the heartbeat signal of the person (i.e. the determining device 26 determines that the potential heartbeat signals are the heartbeat signals). In regard to the potential heartbeat PA1 in FIG. 7, the potential heartbeat signal PC1 and the potential heartbeat signal PB1 exist during the time frame: tA1. Therefore, the determining device 26 determines that the potential heartbeat signals PA1, PB1 and PC1 are the heartbeat signals. Further, how many potential heartbeat signals need to exist during the time frame: tA1 for the determining device 26 to determine that the potential heartbeat signals are the heartbeat signals may be modified.

Subsequently, the determining device 26 executes the same analysis on the potential heartbeat signal PA2 that is subsequently detected by the base piezoelectric sensor 1A and determines whether the potential heartbeat signal PA2 is assumed to be the heartbeat signal. In the example illustrated in FIG. 7, both of the potential heartbeat signals PA2 and PB2 are determined to be the heartbeat signals.

As described above, in a condition where the seating of the person on the seat 2 is determined, whether the potential heartbeat signals are the heartbeat signals or not is determined objectively by comparing time when the potential heartbeat signals, which are detected by the plurality of piezoelectric sensors 1A, 1B, 1C and 1D are appeared. The time frame: tA1 is a time interval in which the potential heartbeat signals can be regarded to be outputted based on the same blood flow. In other words, the time frame: tA1 is defined within a difference of time in which the pulse of the blood flow is transmitted to several piezoelectric sensors 1.

The determining device 26 executes scoring of each of the piezoelectric sensors 1 in order to determine which piezoelectric sensor 1 detects the heartbeat signals of the person in a high frequency among the plurality of piezoelectric sensors 1A, 1B, 1C and 1D provided on the seat 2. More specifically, the determining device 26 provides a point with the piezoelectric sensor 1 that detects the heartbeat signals determined in the manner described above. The heartbeat signal PC1 detected by another piezoelectric sensor 1C exists during a predetermined time frame: tA2 after the peak time of the heartbeat signal PA1 detected by the base piezoelectric sensor 1A. Therefore, each of the piezoelectric sensors 1A and piezoelectric sensor 1C scores the point. In a range illustrated in FIG. 7, the piezoelectric sensor 1A scores one point, the piezoelectric sensor 1B scores zero point, and the piezoelectric sensor 1C scores one point. The scored points are accumulated in each of the piezoelectric sensors. The time frame may be set as follows. The time frame: tA2 ≦tA1 When the heartbeat signal, based on the output signal of one piezoelectric sensor 1 among plurality of piezoelectric sensors 1A, 1B, 1C and 1D, needs to be outputted, the determining device 26 is configured to output the heartbeat signal from the piezoelectric sensor 1 in which the highest score is accumulated.

Figure 8:
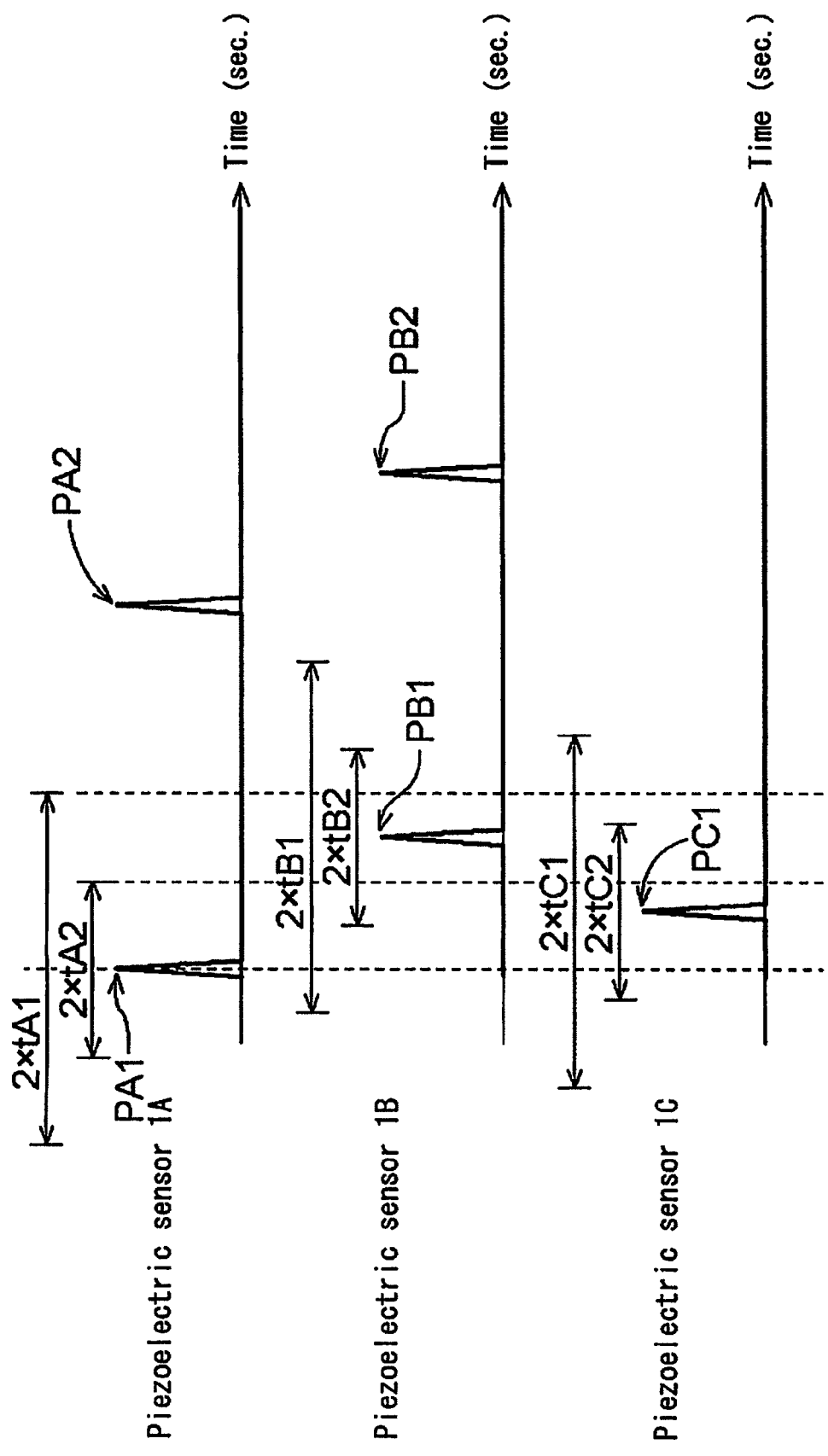
FIG. 8 is a diagram of data on potential heartbeat signals included in output signals of the plurality of piezoelectric sensors provided at the seat, illustrated by each of the piezoelectric sensors.

[Other embodiments][1] In the heartbeat detecting apparatus 20 according to the second embodiment, the determining device 26 determines whether the peak time of another potential heartbeat signal exists during the predetermined time frame after the peak time of the base potential heartbeat signal.However, the heartbeat detecting apparatus 20 may be modified so that the determining device 26 determines whether the peak time of the potential heartbeat signal extracted from the output signal of another piezoelectric sensor exists during a predetermined time frame before and after the peak time of the potential heartbeat signal extracted from the output signal of the base piezoelectric sensor. For example, FIG. 8 is a diagram of data on the potential heartbeat signals included in the output signals of the plurality of piezoelectric sensors provided at the seat, illustrated by each of the piezoelectric sensors. The determining device 26 determines whether the peak time of another potential heartbeat signal exists during the predetermined time frame: 2×tAl (the sum of the time frame: tAl before the peak time and time frame: tAl after the peak time. The same applies hereinbelow) before and after the peak time of the potential heartbeat signal of the base piezoelectric sensor 1A. In the example illustrated in FIG. 8, all of the potential heartbeat signals PA1 PB 1, and PC1 are determined to be the heartbeat signals.

Further, scoring of each of the piezoelectric sensors 1 is executed in the same manner.

More specifically, when the piezoelectric sensor lA is used as the base, the heartbeat signal PC1, detected by another piezoelectric sensor 1C, exists during the predetermined time frame: 2×tA2 (the sum of the time frame before the peak time: tA2 and the time frame after the peak time: tA2. The same applies hereinbelow) before and after the peak time of the heartbeat signal PAL Therefore, each of the piezoelectric sensors 1A and 1C scores the point. Further, when the piezoelectric sensor 1B is used as the base, the heartbeat signal PC1, detected by another piezoelectric sensor 1 C, exists during the predetermined time frame: 2×tB2 before and after the peak time of the heartbeat signal PB 1. Therefore, the piezoelectric sensors 1B and 1C score the point. Furthermore, when the piezoelectric sensor 1C is used as the base, the heartbeat signals PA1 and PB1, detected by other piezoelectric sensors 1 A and 1B, exists during the predetermined time frame: 2×tC2 before and after the peak time of the heartbeat signal PC1. Therefore, the piezoelectric sensors 1 A, 1B and 1C score the point.

[2]

The determining device 26 may be modified so that the determining device 26 executes the above-described determination not only on the peak time of the potential heartbeat signals outputted from the base piezoelectric sensor, but also on the potential heartbeat signals outputted from other piezoelectric sensors. In other words, as illustrated in FIG. 8, the determining device 26 determines whether the peak time of the potential heartbeat signal outputted from another piezoelectric sensor exists during a predetermined time frame: 2×tB1 before and after the peak time of the potential heartbeat signal PB1 of the piezoelectric sensor 1B. When the peak time of potential heartbeat signals outputted from other piezoelectric sensors exist during the time frame: 2×tB1, the potential heartbeat signals PA1 and PC1 existing during the time frame: 2×tB1 are determined to be the heartbeat signals. In the same manner, the determining device 26 determines whether the peak time of the potential heartbeat signal outputted from another piezoelectric sensor exists during predetermined time frame: 2×tC1 before and after the peak time of the potential heartbeat signal PC1 of the piezoelectric sensor 1C. When the peak time of potential heartbeat signals outputted from other piezoelectric sensors exist during the time frame: 2×tC1, the potential heartbeat signals PA1 and PB1 existing during the time frame: 2×tC1 are determined to be the heartbeat signals.

[3]

The determining device 26 may be modified to determine only the potential heartbeat signal outputted from the base piezoelectric sensor to be the heartbeat signal instead of determining all the heartbeat signals existing during the above-described predetermined time to be the heartbeat signals.

In other words, when a second potential heartbeat signal extracted from a second signal component, which is included in the output signal of a second piezoelectric sensor among the plurality of piezoelectric sensors and which exists within the second predetermined frequency range, exists during the predetermined time frame before and after the peak time of a first potential heartbeat signal extracted from a first signal component, which is included in the output signal of the first piezoelectric sensor among the plurality of piezoelectric sensors and which exists within the second predetermined frequency range, and when the signal components, which are included in the output signals of the first and second piezoelectric sensors and which exist within the first frequency range, includes the waveform of the seated person, the determining device 26 may be modified to determine that the first potential heartbeat signal is the heartbeat signal of the person, based on a result of the frequency analysis of the signal processing device executed on each of the output signals of the plurality of piezoelectric sensors.

More specifically, as illustrated in FIG. 8, when the potential heartbeat signal PA1 is used as the base, peak times of other potential heartbeat signals (the second potential heartbeat signals) PB1 and PC1 exist during the predetermined time frame: 2×tAl before and after the peak time of the potential heartbeat signal (the first potential heartbeat signal) PAL The potential heartbeat signals are detected by the piezoelectric sensors 1 that output the signal components determined to include the waveform of the seated person based on the results of frequency analysis and amplitude analysis of the second filter portion 22, the third filter portion 23 and the determining device 26.

The determining device 26 determines that the base potential heartbeat signal PA1 is the heartbeat signal and does not determine that the other potential heartbeat signals PB1 and PC1 are the heartbeat signals. The same applies when the potential heartbeat signal PB1 or PC1 is used as the base. Further, how many potential heartbeat signals need to exist during the predetermined time frame for the determining device 26 to determine that the potential heartbeat signals are the heartbeat signals may be modified.

Further, the determining device 26 may be modified to determine another potential heartbeat signal to be the heartbeat signal instead of determining all of the potential heartbeat signals existing during the predetermined time frame to be the heartbeat signals.

In other words, when a second potential heartbeat signal, extracted from a second signal component which is included in the output signal of second piezoelectric sensor among the plurality of piezoelectric sensors and which exists within the second predetermined frequency range, exists during the predetermined time frame before and after the peak time of a first potential heartbeat signal extracted from a first signal component, which is included in the output signal of the first piezoelectric sensor among the plurality of piezoelectric sensors and which exists within the second predetermined frequency range, and when the signal components, which are included in the output signals of the first and second piezoelectric sensors and which exist within the first frequency range, include the waveform of the seated person, the determining device 26 may be modified to determine that the second potential heartbeat signal is the heartbeat signal of the person, based on a result of the frequency analysis of the signal processing device executed on each of the output signals of the plurality of piezoelectric sensors.

More specifically, as illustrated in FIG. 8, when the potential heartbeat signal PA1 is used as a base, other potential heartbeat signals (the second potential heartbeat signals) PB 1 and PC1 exist during the predetermined time frame: 2×tAl before and after the peak time of the potential heartbeat signal (i.e. the first potential heartbeat signal) PAL The potential heartbeat signals are detected by the piezoelectric sensors 1 that output the signal components that are determined to include the waveform of the seated person based on the results of the frequency analysis and amplitude analysis of the second filter portion 22, the third filter portion 23 and the determining device 26. The determining device 26 determines that the potential heartbeat signals PB1 and PC1, other than the base potential heartbeat signal, to be the heartbeat signals and does not determine that the base potential heartbeat signal PAl to be the heartbeat signal. The same applies when the potential heartbeat signal PB1 or PC1 is used as the base. Further, how many potential heartbeat signals need to exist during the predetermined time frame for the determining device 26 to determine that the potential heartbeat signals are the heartbeat signals may be modified.

[4]

The number of piezoelectric sensors 1 provided relative to the seat 2 and positions of the piezoelectric sensors 1 provided relative to the seat 2 may be modified. For example, the plurality of piezoelectric sensors 1 may be arranged at a portion of the seating portion of the seat 2 where thigh portions of the person contact.

[5]

In the embodiments described above, the first and second frequency ranges may be the same frequency range or a portion of the first frequency range and a portion of the second frequency range may overlap with each other.

INDUSTRIAL APPLICABILITY

The heartbeat detecting apparatus according to the present invention may be used in order to measure the heartbeat without constraining the person.

EXPLANATION FOR REFERENCE NUMBER 1. piezoelectric sensor
2. seat
10. heartbeat detecting apparatus
15. signal processing device
16. determining device
20. heartbeat detecting apparatus
25. signal processing device
26. determining device

The invention claimed is:

1. A heartbeat detecting apparatus comprising:
a plurality of piezoelectric sensors providing output signals;
a seat containing the plurality of piezoelectric sensors;
each output signal including a signal component;
a signal processing device that executes a frequency analysis separately on the respective output signals to provide a result; and
a determining device that
determines that the signal component of each of two or more of the output signals includes a waveform of a seated person indicating that a person is seated on the seat, based on the result of the frequency analysis, when the signal component exists within a first predetermined frequency range and within a predetermined amplitude range,
determines that the signal component of each of the two or more output signals is a potential heartbeat signal when the signal component exists within a second predetermined frequency range and during a predetermined time frame, and
determines that at least one of the potential heartbeat signals is a heartbeat signal of a person when the signal component of each of the two or more of the output signals includes a waveform of a seated person and is determined to be a potential heartbeat signal.

2. The heartbeat detecting apparatus according to claim 1, further comprising:
a filter portion eliminating another signal component, existing within a frequency range of a vehicle vibration, from the output signals of the piezoelectric sensors.

3. A heartbeat detecting apparatus comprising:
a plurality of piezoelectric sensors providing output signals;
a seat containing the plurality of piezoelectric sensors;
each output signal including a signal component;
a signal processing device that executes a frequency analysis separately on the respective output signals to provide a result; and
a determining device that
determines that the signal component of each of two or more of the output signals include a waveform of a seated person indicating that a person is seated on the seat, based on a result of the frequency analysis,
determines that the signal component of each of two or more of the output signals is a potential heartbeat signal when the signal component exists within a predetermined frequency range and during a predetermined time frame, and
determines that at least one of the potential heartbeat signals is a heartbeat signal of a person when the signal components of each of the two or more of the output signals includes a waveform of a seated person and are determined to be potential heartbeat signals.

4. The heartbeat detecting apparatus according to claim 3, further comprising:
a filter portion eliminating another signal component, existing within a frequency range of a vehicle vibration, from the output signals of the piezoelectric sensors.

5. A heartbeat detecting apparatus comprising:
a first piezoelectric sensor and a second piezoelectric sensor providing a first output signal and a second output signal, respectively;
a seat containing the first piezoelectric sensor and the second piezoelectric sensor;
the first output signal including a first signal component, and the second output signal including a second output component;
a signal processing device that executes a frequency analysis separately on the respective output signals to provide a result; and
a determining device determines that a first potential heartbeat signal is a heartbeat signal of the human body when
based on the result of the frequency analysis, each of the first signal component and the second signal component includes a waveform that exists within a first predetermined frequency range and within a predetermined amplitude range indicative that a person is seated on the seat, and
the second potential heartbeat signal extracted from the second signal component, which exists within a second predetermined frequency range, exists during a predetermined time frame before or after a peak time of the first potential heartbeat signal, which is extracted from the first signal component and exists within the second predetermined frequency range.

6. The heartbeat detecting apparatus according to claim 5, further comprising:
a filter portion eliminating another signal component, existing within a frequency range of a vehicle vibration, from the output signals of the piezoelectric sensors.

7. A heartbeat detecting apparatus comprising:
a first piezoelectric sensor and a second piezoelectric sensor providing a first output signal and a second output signal, respectively;
a seat containing the first piezoelectric sensor and the second piezoelectric sensor;
the first output signal including a first signal component, and the second output signal including a second output component;
a signal processing device that executes a frequency analysis separately on the respective output signals to provide a result; and
a determining device determines that a second potential heartbeat signal is a heartbeat signal of the human body when
based on the result of the frequency analysis, each of the first signal component and the second signal component includes a waveform that exists within a first predetermined frequency range and within a predetermined amplitude range indicative that a person is seated on the seat, and the second potential heartbeat signal extracted from the second signal component, which exists within a second predetermined frequency range, exists during a predetermined time frame before or after a peak time of the first potential heartbeat signal, which is extracted from the first signal component and exists within the second predetermined frequency range.

8. The heartbeat detecting apparatus according to claim 7, further comprising:
a filter portion eliminating another signal component, existing within a frequency range of a vehicle vibration, from the output signals of the piezoelectric sensors.

9. A heartbeat detecting apparatus comprising:
a plurality of piezoelectric sensors providing output signals;
a seat containing the plurality of piezoelectric sensors;
each output signal including a signal component;
a signal processing device that executes a frequency analysis separately on the respective output signals; and
a determining device that
determines that the signal component of each of two or more of the output signals includes a waveform of a seated person indicating that a person is seated on the seat, based on the result of the frequency analysis, when the signal component exists within a first predetermined frequency range and within a predetermined amplitude range, determines that the signal component of each of the two or more output signals is a potential heartbeat signal when the signal component exists within a second predetermined frequency range and during a predetermined time frame, determines that each of the potential heartbeat signals is a heartbeat signal of a person when the signal components of each of the two or more of the output signals includes a waveform of a seated person and are determined to be potential heartbeat signals;

provides a point to a base piezoelectric sensor and to another piezoelectric sensor whenever the heartbeat signal detected by the other piezoelectric sensor exists during a predetermined time frame before or after a peak time of the heartbeat signal detected by the base piezoelectric sensor, so that points are accumulated by each of the piezoelectric sensors, and outputs the heartbeat signal of the of the piezoelectric sensor in which the highest number of points is accumulated.

10. The heartbeat detecting apparatus according to claim 9, further comprising:
a filter portion eliminating another signal component, existing within a frequency range of a vehicle vibration, from the output signals of the piezoelectric sensors.

* * * * *